(12) United States Patent
Brodmann et al.

(10) Patent No.: US 8,017,359 B2
(45) Date of Patent: Sep. 13, 2011

(54) METHODS AND KITS PERTAINING TO THE DETECTION, IDENTIFICATION AND QUANTIFICATION OF BACTERIA AND YEAST IN WINE, BEER AND JUICES

(75) Inventors: Peter D. Brodmann, Liestal (CH); Marc Fehlmann, Waedenswil (CH); Juerg Gafner, Waedenswil (CH); Naomi Porret, Zurich (CH); Sergio Schmid, Glis (CH); Ralf Seyfarth, Binningen (CH); Martin Sievers, Waedenswil (CH); Anne Terrettaz, Sierre (CH); Christina Uermoesi, Waedenswil (CH)

(73) Assignee: ETS Laboratories, St. Helena, CA (US)

( * ) Notice: Subject to any disclaimer, the term of this patent is extended or adjusted under 35 U.S.C. 154(b) by 986 days.

(21) Appl. No.: 11/571,086

(22) PCT Filed: Jun. 6, 2005

(86) PCT No.: PCT/EP2005/006044
§ 371 (c)(1),
(2), (4) Date: Oct. 31, 2007

(87) PCT Pub. No.: WO2005/123943
PCT Pub. Date: Dec. 29, 2005

(65) Prior Publication Data
US 2008/0268430 A1    Oct. 30, 2008

(30) Foreign Application Priority Data
Jun. 21, 2004 (EP) .................................... 04014518

(51) Int. Cl.
C12Q 1/68 (2006.01)
C12P 19/34 (2006.01)
C07H 21/04 (2006.01)

(52) U.S. Cl. ......... 435/91.2; 435/6; 435/91.1; 536/24.3; 536/24.33

(58) Field of Classification Search ................. None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis et al. |
| 4,800,159 A | 1/1989 | Mullis et al. |
| 5,210,015 A | 5/1993 | Gelfand et al. |
| 6,248,519 B1 | 6/2001 | Morenzoni et al. |

OTHER PUBLICATIONS

Phister et al., "Real-Time PCR Assay for Detection and Enumeration of Dekkera bruxellensis in Wine," Applied and Environmental Microbiology, Dec. 2003, vol. 69, No. 12, pp. 7430-7434.*
Pai S.R. et al. "Identification of viable and non-viable Mycobacterium tuberculosis in mouse organs by directed RT-PCR for antigen 85B mRNA." in Microbial Pathogenesis, vol. 28, No. 6, Jun. 2000, pp. 335-342.
Bleve Gianluca et al. "Development of reverse transcription (RT)-PCR and real-time RT-PCR assays for rapid detection and quantification of viable yeasts and molds contaminating yogurts and pasteurized food products." in Applied and Environmental Microbiology, vol. 69, No. 7, Jul. 2000, pp. 4116-4122.
Phister Trevor G. et al.: "Real-time PCR assay for detection and enumeration of Dekkera bruxellensis in wine." in Applied and Environmental Microbiology, vol. 69, No. 12, Dec. 2003, pp. 7430-7434.
Satokari R. et al.: "Detection of beer spoilage bacteria Megasphaera and Pectinatus by polymerase chain reaction and colorimetric microplate hybridization" in International Journal of Food Microbiology, Elsevier Science Publishers, Amsterdam, NL,vol. 45, No. 2, 1998, pp. 119-127.
Casey Garrett D. et al.: "Potential of using real-time PCR-based detection of spoilage yeast in fruit juice: A preliminary study." in International Journal of Food Microbiology, vol. 91, No. 3, Mar. 15, 2004, pp. 327-335.
Kosse D. et al.: "Identification of yoghurt-spoiling yeast with 18S RRNA-targeted oligonucleotide porbes" in Systematic and Applied Microbiology, vol. 20, 1997, pp. 468-480.
Database EMBL, Jul. 13, 1992; Accession No. D12534.
Database EMBL, Jul. 31, 1991; Accession No. L00026.

* cited by examiner

*Primary Examiner* — Young J Kim
(74) *Attorney, Agent, or Firm* — Joyce von Natzmer Pequignot + Myers LLC

(57) ABSTRACT

The invention concerns new analytical methods for detecting and identifying qualitatively and quantitatively germ contaminations, e.g. bacterial and yeast contaminations usings specific DNA sequences, indicating living and dead germs within 12 hours time or less. The DNA is amplified and as quantified. The invention also embraces kits.

5 Claims, No Drawings

SEQUENCE LISTING

<160> NUMBER OF SEQ ID NOS: 48

<210> SEQ ID NO 1
<211> LENGTH: 64
<212> TYPE: DNA
<213> ORGANISM: Dekkera bruxellensis
<220> FEATURE:
<221> NAME/KEY: primer_bind
<222> LOCATION: (1)..(64)
<223> OTHER INFORMATION: complete amplicon sequence

<400> SEQUENCE: 1
tgtcagagac atcaaggaga agctttgtta cgttgctttg gactttgacc aggaaatgca    60
gacg                                                                64

<210> SEQ ID NO 2
<211> LENGTH: 24
<212> TYPE: DNA
<213> ORGANISM: Dekkera bruxellensis
<220> FEATURE:
<221> NAME/KEY: primer_bind

```
<222> LOCATION: (1)..(24)
<223> OTHER INFORMATION: forward primer

<400> SEQUENCE: 2
tgtcagagac atcaaggaga agct                                          24

<210> SEQ ID NO 3
<211> LENGTH: 18
<212> TYPE: DNA
<213> ORGANISM: Dekkera bruxellensis
<220> FEATURE:
<221> NAME/KEY: primer_bind
<222> LOCATION: (1)..(18)
<223> OTHER INFORMATION: MGB probe

<400> SEQUENCE: 3
tgttacgttg ctttggac                                                 18

<210> SEQ ID NO 4
<211> LENGTH: 20
<212> TYPE: DNA
<213> ORGANISM: Dekkera bruxellensis
<220> FEATURE:
<221> NAME/KEY: primer_bind
<222> LOCATION: (1)..(20)
<223> OTHER INFORMATION: reverse primer

<400> SEQUENCE: 4
cgtctgcatt tcctggtcaa                                               20

<210> SEQ ID NO 5
<211> LENGTH: 73
<212> TYPE: DNA
<213> ORGANISM: Dekkera bruxellensis
<220> FEATURE:
<221> NAME/KEY: primer_bind
<222> LOCATION: (1)..(73)
<223> OTHER INFORMATION: complete amplicon sequence

<400> SEQUENCE: 5
tgtcagagac atcaaggaga agctttgtta cgttgctttg gactttgacc aggaaatgca   60
gacggcagca cag                                                      73

<210> SEQ ID NO 6
<211> LENGTH: 24
<212> TYPE: DNA
<213> ORGANISM: Dekkera bruxellensis
<220> FEATURE:
<221> NAME/KEY: primer_bind
<222> LOCATION: (1)..(24)
<223> OTHER INFORMATION: forward primer

<400> SEQUENCE: 6
tgtcagagac atcaaggaga agct                                          24

<210> SEQ ID NO 7
<211> LENGTH: 29
<212> TYPE: DNA
<213> ORGANISM: Dekkera bruxellensis
<220> FEATURE:
<221> NAME/KEY: primer_bind
<222> LOCATION: (1)..(29)
<223> OTHER INFORMATION: TaqMan probe

<400> SEQUENCE: 7
tgttacgttg ctttggactt tgaccagga                                     29
```

```
<210> SEQ ID NO 8
<211> LENGTH: 18
<212> TYPE: DNA
<213> ORGANISM: Dekkera bruxellensis
<220> FEATURE:
<221> NAME/KEY: primer_bind
<222> LOCATION: (1)..(18)
<223> OTHER INFORMATION: reverse primer

<400> SEQUENCE: 8
ctgtgctgcc gtctgcat                                                   18

<210> SEQ ID NO 9
<211> LENGTH: 68
<212> TYPE: DNA
<213> ORGANISM: Hanseniaspora uvarum
<220> FEATURE:
<221> NAME/KEY: primer_bind
<222> LOCATION: (1)..(68)
<223> OTHER INFORMATION: complete amplicon sequence

<400> SEQUENCE: 9
tcaaagaaaa gttatcytac gttgctttag actttgacca agaaatggaa actgctgctc    60
aatcttca                                                              68

<210> SEQ ID NO 10
<211> LENGTH: 27
<212> TYPE: DNA
<213> ORGANISM: Hanseniaspora uvarum
<220> FEATURE:
<221> NAME/KEY: primer_bind
<222> LOCATION: (1)..(27)
<223> OTHER INFORMATION: forward primer

<400> SEQUENCE: 10
tcaaagaaaa gttatcytac gttgctt                                         27

<210> SEQ ID NO 11
<211> LENGTH: 17
<212> TYPE: DNA
<213> ORGANISM: Hanseniaspora uvarum
<220> FEATURE:
<221> NAME/KEY: primer_bind
<222> LOCATION: (1)..(17)
<223> OTHER INFORMATION: MGB probe

<400> SEQUENCE: 11
agactttgac caagaaa                                                    17

<210> SEQ ID NO 12
<211> LENGTH: 22
<212> TYPE: DNA
<213> ORGANISM: Hanseniaspora uvarum
<220> FEATURE:
<221> NAME/KEY: primer_bind
<222> LOCATION: (1)..(20)
<223> OTHER INFORMATION: reverse primer

<400> SEQUENCE: 12
tgaagattga gcagcagttt cc                                              22

<210> SEQ ID NO 13
<211> LENGTH: 81
<212> TYPE: DNA
<213> ORGANISM: Hanseniaspora uvarum
<220> FEATURE:
<221> NAME/KEY: primer_bind
<222> LOCATION: (1)..(81)
<223> OTHER INFORMATION: complete amplicon sequence
```

```
<400> SEQUENCE: 13
agtcatcacc attggtaacg aaagattcag agctccagaa gccttattcc aaccttcctt    60
tattggttta gaatctgctg g                                              81

<210> SEQ ID NO 14
<211> LENGTH: 24
<212> TYPE: DNA
<213> ORGANISM: Hanseniaspora uvarum
<220> FEATURE:
<221> NAME/KEY: primer_bind
<222> LOCATION: (1)..(24)
<223> OTHER INFORMATION: forward primer

<400> SEQUENCE: 14
agtcatcacc attggtaacg aaag                                           24

<210> SEQ ID NO 15
<211> LENGTH: 30
<212> TYPE: DNA
<213> ORGANISM: Hanseniaspora uvarum
<220> FEATURE:
<221> NAME/KEY: primer_bind
<222> LOCATION: (1)..(30)
<223> OTHER INFORMATION: TaqMan probe

<400> SEQUENCE: 15
ttcagagctc cagaagcctt attccaacct                                     30

<210> SEQ ID NO 16
<211> LENGTH: 25
<212> TYPE: DNA
<213> ORGANISM: Hanseniaspora uvarum
<220> FEATURE:
<221> NAME/KEY: primer_bind
<222> LOCATION: (1)..(25)
<223> OTHER INFORMATION: reverse primer

<400> SEQUENCE: 16
ccagcagatt ctaaaccaat aaagg                                          25

<210> SEQ ID NO 17
<211> LENGTH: 90
<212> TYPE: DNA
<213> ORGANISM: Pediococcus damnosus
<220> FEATURE:
<221> NAME/KEY: primer_bind
<222> LOCATION: (1)..(90)
<223> OTHER INFORMATION: complete amplicon sequence

<400> SEQUENCE: 17
aggaatggat gaattgtctg atgaagagaa gacaatcgtt ggacgtgctc gtagaattca    60
gttcttcttg tcacagaatt tctctgttgc                                     90

<210> SEQ ID NO 18
<211> LENGTH: 24
<212> TYPE: DNA
<213> ORGANISM: Pediococcus damnosus
<220> FEATURE:
<221> NAME/KEY: primer_bind
<222> LOCATION: (1)..(24)
<223> OTHER INFORMATION: forward primer

<400> SEQUENCE: 18
aggaatggat gaattgtctg atga                                           24
```

```
<210> SEQ ID NO 19
<211> LENGTH: 30
<212> TYPE: DNA
<213> ORGANISM: Pediococcus damnosus
<220> FEATURE:
<221> NAME/KEY: primer_bind
<222> LOCATION: (1)..(30)
<223> OTHER INFORMATION: TaqMan probe

<400> SEQUENCE: 19
atcgttggac gtgctcgtag aattcagttc                                         30

<210> SEQ ID NO 20
<211> LENGTH: 25
<212> TYPE: DNA
<213> ORGANISM: Pediococcus damnosus
<220> FEATURE:
<221> NAME/KEY: primer_bind
<222> LOCATION: (1)..(25)
<223> OTHER INFORMATION: reverse primer

<400> SEQUENCE: 20
gcaacagaga aattctgtga caaga                                              25

<210> SEQ ID NO 21
<211> LENGTH: 65
<212> TYPE: DNA
<213> ORGANISM: Pediococcus parvulus
<220> FEATURE:
<221> NAME/KEY: primer_bind
<222> LOCATION: (1)..(65)
<223> OTHER INFORMATION: complete amplicon sequence

<400> SEQUENCE: 21
tcaagaaacc agacggcagt attttggttg ctgaagtcgc tcttgaactt ggagacggcg        60
ttgtg                                                                   65

<210> SEQ ID NO 22
<211> LENGTH: 23
<212> TYPE: DNA
<213> ORGANISM: Pediococcus parvulus
<220> FEATURE:
<221> NAME/KEY: primer_bind
<222> LOCATION: (1)..(23)
<223> OTHER INFORMATION: forward primer

<400> SEQUENCE: 22
tcaagaaacc agacggcagt att                                                23

<210> SEQ ID NO 23
<211> LENGTH: 21
<212> TYPE: DNA
<213> ORGANISM: Pediococcus parvulus
<220> FEATURE:
<221> NAME/KEY: primer_bind
<222> LOCATION: (1)..(21)
<223> OTHER INFORMATION: TaqMan probe

<400> SEQUENCE: 23
tggttgctga agtcgctctt g                                                  21

<210> SEQ ID NO 24
<211> LENGTH: 19
<212> TYPE: DNA
<213> ORGANISM: Pediococcus parvulus
<220> FEATURE:
<221> NAME/KEY: primer_bind
<222> LOCATION: (1)..(19)
<223> OTHER INFORMATION: reverse primer
```

-continued

```
<400> SEQUENCE: 24
cacaacgccg tctccaagt                                                19

<210> SEQ ID NO 25
<211> LENGTH: 64
<212> TYPE: DNA
<213> ORGANISM: Pediococcus pentosaceus
<220> FEATURE:
<221> NAME/KEY: primer_bind
<222> LOCATION: (1)..(64)
<223> OTHER INFORMATION: complete amplicon sequence

<400> SEQUENCE: 25
ctatcgatgg cggcaaagaa cttggccccg atataaaacg cgatccaatc catcgtgatc    60
cacc                                                                64

<210> SEQ ID NO 26
<211> LENGTH: 19
<212> TYPE: DNA
<213> ORGANISM: Pediococcus pentosaceus
<220> FEATURE:
<221> NAME/KEY: primer_bind
<222> LOCATION: (1)..(19)
<223> OTHER INFORMATION: forward primer

<400> SEQUENCE: 26
ctatcgatgg cggcaaaga                                                19

<210> SEQ ID NO 27
<211> LENGTH: 22
<212> TYPE: DNA
<213> ORGANISM: Pediococcus pentosaceus
<220> FEATURE:
<221> NAME/KEY: primer_bind
<222> LOCATION: (1)..(22)
<223> OTHER INFORMATION: TaqMan probe

<400> SEQUENCE: 27
cttggccccg atataaaacg cg                                            22

<210> SEQ ID NO 28
<211> LENGTH: 18
<212> TYPE: DNA
<213> ORGANISM: Pediococcus pentosaceus
<220> FEATURE:
<221> NAME/KEY: primer_bind
<222> LOCATION: (1)..(18)
<223> OTHER INFORMATION: reverse primer

<400> SEQUENCE: 28
ggtggatcac gatggatt                                                 18

<210> SEQ ID NO 29
<211> LENGTH: 66
<212> TYPE: DNA
<213> ORGANISM: Lactobacillus brevis
<220> FEATURE:
<221> NAME/KEY: primer_bind
<222> LOCATION: (1)..(66)
<223> OTHER INFORMATION: complete amplicon sequence

<400> SEQUENCE: 29
ggtgcttcga tttctgttcc agtcggtgac gatacccttg gtcgggtgtt caacgtgctc    60
ggggat                                                              66
```

-continued

```
<210> SEQ ID NO 30
<211> LENGTH: 21
<212> TYPE: DNA
<213> ORGANISM: Lactobacillus brevis
<220> FEATURE:
<221> NAME/KEY: primer_bind
<222> LOCATION: (1)..(21)
<223> OTHER INFORMATION: forward primer

<400> SEQUENCE: 30
ggtgcttcga tttctgttcc a                                              21

<210> SEQ ID NO 31
<211> LENGTH: 23
<212> TYPE: DNA
<213> ORGANISM: Lactobacillus brevis
<220> FEATURE:
<221> NAME/KEY: primer_bind
<222> LOCATION: (1)..(23)
<223> OTHER INFORMATION: TaqMan probe

<400> SEQUENCE: 31
cggtgacgat acccttggtc ggg                                            23

<210> SEQ ID NO 32
<211> LENGTH: 18
<212> TYPE: DNA
<213> ORGANISM: Lactobacillus brevis
<220> FEATURE:
<221> NAME/KEY: primer_bind
<222> LOCATION: (1)..(18)
<223> OTHER INFORMATION: reverse primer

<400> SEQUENCE: 32
atccccgagc acgttgaa                                                  18

<210> SEQ ID NO 33
<211> LENGTH: 76
<212> TYPE: DNA
<213> ORGANISM: Lactobacillus hilgardii
<220> FEATURE:
<221> NAME/KEY: primer_bind
<222> LOCATION: (1)..(76)
<223> OTHER INFORMATION: complete amplicon sequence

<400> SEQUENCE: 33
gatggtgttg tgcgaacgat cgcgatggat ggaaccgatg gtcttcgtcg tggaatggaa    60
gttgaaaata ctgatt                                                    76

<210> SEQ ID NO 34
<211> LENGTH: 20
<212> TYPE: DNA
<213> ORGANISM: Lactobacillus hilgardii
<220> FEATURE:
<221> NAME/KEY: primer_bind
<222> LOCATION: (1)..(19)
<223> OTHER INFORMATION: forward primer

<400> SEQUENCE: 34
gatggtgttg tgcgaacgat                                                20

<210> SEQ ID NO 35
<211> LENGTH: 25
<212> TYPE: DNA
<213> ORGANISM: Lactobacillus hilgardii
<220> FEATURE:
<221> NAME/KEY: primer_bind
<222> LOCATION: (1)..(25)
<223> OTHER INFORMATION: TaqMan probe
```

```
<400> SEQUENCE: 35
cgatggatgg aaccgatggt cttcg                                          25

<210> SEQ ID NO 36
<211> LENGTH: 26
<212> TYPE: DNA
<213> ORGANISM: Lactobacillus hilgardii
<220> FEATURE:
<221> NAME/KEY: primer_bind
<222> LOCATION: (1)..(26)
<223> OTHER INFORMATION: reverse primer

<400> SEQUENCE: 36
aatcagtatt ttcaacttcc attcca                                         26

<210> SEQ ID NO 37
<211> LENGTH: 123
<212> TYPE: DNA
<213> ORGANISM: Saccharomyces bayanus
<220> FEATURE:
<221> NAME/KEY: primer_bind
<222> LOCATION: (1)..(123)
<223> OTHER INFORMATION: complete amplicon sequence

<400> SEQUENCE: 37
atttggccgg tagagatttg actgactact tgatgaagat cttgagtgaa cgtggttact    60
ctttctccac cactgctgaa agagaaattg tccgtgacat caaggaaaaa ctatgttacg   120
tcg                                                                 123

<210> SEQ ID NO 38
<211> LENGTH: 22
<212> TYPE: DNA
<213> ORGANISM: Saccharomyces bayanus
<220> FEATURE:
<221> NAME/KEY: primer_bind
<222> LOCATION: (1)..(22)
<223> OTHER INFORMATION: forward primer

<400> SEQUENCE: 38
atttggccgg tagagatttg ac                                             22

<210> SEQ ID NO 39
<211> LENGTH: 33
<212> TYPE: DNA
<213> ORGANISM: Saccharomyces bayanus
<220> FEATURE:
<221> NAME/KEY: primer_bind
<222> LOCATION: (1)..(33)
<223> OTHER INFORMATION: TaqMan probe

<400> SEQUENCE: 39
ttgagtgaac gtggttactc tttctccacc act                                 33

<210> SEQ ID NO 40
<211> LENGTH: 33
<212> TYPE: DNA
<213> ORGANISM: Saccharomyces bayanus
<220> FEATURE:
<221> NAME/KEY: primer_bind
<222> LOCATION: (1)..(33)
<223> OTHER INFORMATION: reverse primer

<400> SEQUENCE: 40
ttgagtgaac gtggttactc tttctccacc act                                 33
```

```
<210> SEQ ID NO 41
<211> LENGTH: 82
<212> TYPE: DNA
<213> ORGANISM: Saccharomyces spp
<220> FEATURE:
<221> NAME/KEY: primer_bind
<222> LOCATION: (1)..(82)
<223> OTHER INFORMATION: complete amplicon sequence

<400> SEQUENCE: 41
ttgagagttg ccccagaaga acaccctgtt cttttgactg aagctccaat gaaccctaaa    60
tcaaacagag aaaagatgac tc                                             82

<210> SEQ ID NO 42
<211> LENGTH: 22
<212> TYPE: DNA
<213> ORGANISM: Saccharomyces spp
<220> FEATURE:
<221> NAME/KEY: primer_bind
<222> LOCATION: (1)..(22)
<223> OTHER INFORMATION: forward primer

<400> SEQUENCE: 42
ttgagagttg ccccagaaga ac                                             22

<210> SEQ ID NO 43
<211> LENGTH: 16
<212> TYPE: DNA
<213> ORGANISM: Saccharomyces spp
<220> FEATURE:
<221> NAME/KEY: primer_bind
<222> LOCATION: (1)..(16)
<223> OTHER INFORMATION: MGB probe

<400> SEQUENCE: 43
accctgttct tttgac                                                    16

<210> SEQ ID NO 44
<211> LENGTH: 28
<212> TYPE: DNA
<213> ORGANISM: Saccharomyces spp
<220> FEATURE:
<221> NAME/KEY: primer_bind
<222> LOCATION: (1)..(28)
<223> OTHER INFORMATION: reverse primer

<400> SEQUENCE: 44
gagtcatctt ttctctgttt gatttagg                                       28

<210> SEQ ID NO 45
<211> LENGTH: 78
<212> TYPE: DNA
<213> ORGANISM: Oenococcus oeni
<220> FEATURE:
<221> NAME/KEY: primer_bind
<222> LOCATION: (1)..(78)
<223> OTHER INFORMATION: complete amplicon sequence

<400> SEQUENCE: 45
tggattgact cgtggcatga aggttcttga taccggtgct cctattgaag ttccggttgg    60
agaagcgacg ttgggacg                                                  78

<210> SEQ ID NO 46
<211> LENGTH: 20
<212> TYPE: DNA
<213> ORGANISM: Oenococcus oeni
<220> FEATURE:
<221> NAME/KEY: primer_bind
```

```
<222> LOCATION: (1)..(20)
<223> OTHER INFORMATION: forward primer

<400> SEQUENCE: 46
tggattgact cgtggcatga                                              20

<210> SEQ ID NO 47
<211> LENGTH: 28
<212> TYPE: DNA
<213> ORGANISM: Oenococcus oeni
<220> FEATURE:
<221> NAME/KEY: primer_bind
<222> LOCATION: (1)..(28)
<223> OTHER INFORMATION: TaqMan probe

<400> SEQUENCE: 47
tgataccggt gctcctattg aagttccg                                     28

<210> SEQ ID NO 48
<211> LENGTH: 18
<212> TYPE: DNA
<213> ORGANISM: Oenococcus oeni
<220> FEATURE:
<221> NAME/KEY: primer_bind
<222> LOCATION: (1)..(18)
<223> OTHER INFORMATION: reverse primer

<400> SEQUENCE: 48
cgtcccaacg tcgcttct                                                18
```

METHODS AND KITS PERTAINING TO THE DETECTION, IDENTIFICATION AND QUANTIFICATION OF BACTERIA AND YEAST IN WINE, BEER AND JUICES

This is the U.S. national stage of International application PCT/EP2005/006044, filed Jun. 6, 2005 designating the United States.

FIELD OF THE INVENTION

The invention concerns new analytical methods to detect and identify germ contamination, e.g. bacterial and yeast contaminations, preferably such that spoil food and beverage samples. Furthermore the invention describes new analytical methods to detect and identify desired yeast organism, which appear in alcoholic and non-alcoholic beverages. The invention also embraces test kits.

The new invented analytical methods and test kits qualitatively and quantitatively detect and identify microbial contamination and desired micro-organisms using specific DNA sequences, indicating living and dead germs within 12 hours. The DNA is amplified and as such quantified. Those methods being inventive will replace conventional analytical methods like cultivation and microscopy methods, GC-MS or so-called fast detection tests later described.

It is very well-known that the manufacture of food and beverage requires very strictly environmental control of the starting, intermediate and final products for their quality in chemical, physical over all microbiological aspects. Otherwise, sensory deficiencies might show up and could cause drastic financial damages.

BACKGROUND

The determination of germs, desired and undesired micro-organisms via microscopy occurred after cultivation on suitable media and by conventional microscopically counting of germs. The use of a microscopy permits to distinguish between micro-organisms and turbidity (e.g. tanning agent), a morphological identification of the micro-organism and a rough estimation of living and dead micro-organism.

This method is known since long and very well described in literature, but bears some disadvantages, such as lack of precision, high degree of manually performed procedures which are difficult to be automated. Furthermore limit is up to 10000 germs/ml.

An alternative microbiological method of the specific determination of germs is based on the growth of those germs on specific media and subsequent determination of the micro-organisms via microscopy. Methods of that kind are commercially available. The application of the specific method however, has substantially the same disadvantages as the above described method for the total count of viable cells. A further disadvantage is the long incubation time of at least 48 hours.

A further method to determine germs is based via biochemical reactions after cultivation on suitable media and total viable count of desired and undesired micro-organism.

Biochemical reactions (as e.g. the API test of Biomerieux) allows distinguishing between different micro-organism. This well known method bears the disadvantage that a high degree of manually performed procedures are necessary, which are difficult to be automated. Furthermore a clear identification of micro-organism is not possible in a mixture of different micro-organisms and cannot be used as a quantitative assay.

Further detection of some micro-organisms may occur by GC/MS or LC/MS by using some secondary metabolites that are synthesized by particular micro-organism. Such metabolites can be detected using a chromatographic separation and a subsequent determination using for example mass spectrometry or spectrophotometrical detection.

One important example in the wine producing industry is for example the repeating detection of the secondary metabolites 4-ethylphenol and 4-ethyl-guajacol which serves as an indication for the presence of *Dekkera bruxellensis*. As already mentioned above the detection using GC/MS or LC/MS is a rather expensive method. The detection using secondary metabolites cannot be allocated to a unique micro-organism. Furthermore the production of secondary metabolites is strongly dependent on environmental conditions and is therefore not really suitable for quantitative determination.

The newly upcoming PCR Technology (for qualitative use) itself is based on the presence of DNA. The DNA either already exists in single strands or the DNA coil is split into single strands. Two oligonucletide-primers are added in excess. They dock onto a specific part of the DNA not too distant apart from each other and in presence of an initializer for polymerization of nucleotides (polymerase) the specific segment defined/between the primers is replicated. When starting from a single DNA coil, i.e. of two strings, after polymerisation two new coils, i.e. four strings of identical composition are formed. Thereafter those can be used to be replicated in a other cycle. If these steps are reproduced, they lead to an exponential increase of the presence of this specific segment of DNA.

The quantitative PCR method is an improved methodology based on creating an oligonucleotide-probe that fits between the two primers and sits on the segment top be replicated. This methodology is based on the TaqMan®-Technology, which is based on the 5'-nuclease 'PCR assay, published in 1991 by Holland et al., exploiting the 5'-nuclease activity of the TaqPolymerase and the application of fluorescence marked and sequences specific probes.

Those probes are labelled at the 5'-terminal with a fluorescing agent (reporter) and at the 3'-terminal with a fluorescence quencher (quencher).

As the space between them is restricted, the fluorescence emitted by the reporter is quenched by the quencher (or dark quencher) so no fluorescence can be observed. During the polymerase induced chain reaction both the reporter and the quencher or dark quencher, respectively, are released from their positions and are no longer staying close together but are in solution. Under these circumstances, a resulting fluorescence of the reporter can be recorded. The more reporter molecules are released, the higher the intensity of the fluorescence signal results. The quantity of the fluorescence signal is proportional to the amount of sequences replicated. By an analysis of the kinetics, i.e. the number of cycles l needed to obtain a certain signal the initial number of copies of that sequence can be calculated.

This method is extremely sensitive as it replicates the sequences present and hence intensifies the signal to be recorded with each cycle. There are many molecules that show molecules fluorescence under different conditions, which allow to design internal standards that control the success of each replication. Furthermore it is possible to test for the presence of different sequences in parallel using different wavelength to detect the resulting fluorescence of each one.

The optimisation of primer and probe pairs and the variable reaction conditions of the PCR method is essential. The PCR-technology is executed corresponding to the methods described in U.S. Pat. No. 4,683,195, U.S. Pat. No. 4,683,202 and U.S. Pat. No. 4,800,159.

U.S. Pat. No. 4,683,195 is directed to a process for amplifying and detecting any target nucleic acid contained in a nucleic acid or mixture thereof. The process comprises treating separate complementary strands of the nucleic acid with a molar excess of two oligonucleotide primers, extending the primers to form complementary primer extension products which act as templates for synthesizing the desired nucleic acid sequence, and detecting the sequence so amplified. The steps of the reaction may be carried out stepwise or simultaneously and can be repeated as often as desired.

U.S. Pat. No. 4,683,202 is directed to a process for amplifying any desired specific nucleic acid sequence contained in nucleic acid or mixture thereof.

The process comprises treating separate complementary strands of the nucleic acid with a molar excess of two oligonucleotide primers, and extending the primers to form complementary primer extension products which act as templates for synthesizing the desired nucleic acid sequence. The steps of the reaction may be carried out stepwise or simultaneously and can be repeated as often as desired.

U.S. Pat. No. 4,800,159 claims a process for amplifying and detecting any target nucleic acid sequence contained in a nucleic acid or mixture thereof. The process comprises treating separate complementary strands of the nucleic acid with a molar excess of two oligonucleotide primers in the same manner as described above. In addition, a specific nucleic acid sequence may be cloned into a vector by using primers to amplify the sequence, which contain restriction sites on their non-complementary ends, and a nucleic acid fragment may be prepared from an existing shorter fragment using the amplification process.

U.S. Pat. No. 5,210,015 referring to the three above mentioned US patents is directed to a process of detecting a target nucleic acid using labelled oligonucleotides. This process uses the 5' to 3' nuclease activity of a nucleic acid polymerase to cleave annealed labelled oligonucleotide from hybridized duplexes and release labelled oligonucleotide fragments for detection. This can easily be incorporated into a PCR amplification assay.

G. Zapparoli et al. reported in Letters in Applied Microbiology/1998, 27, 243-245 on rapid identification and detection of *Oenococcus oeni* in wine achieved by specific PCR. Two primers flanking a 1025 bp region of the *O. oeni* gene encoding the malolactic enzyme were designed. The expected DNA amplificate was obtained only when purified DNA *O. oeni* was used.

The rapidity and reliability of the PCR procedure established suggests that the method may be profitably applied in winery laboratories for quality control. It has been suggested that the use of above mentioned PCR amplification procedure might also prove useful for the rapid and reliable identification/detection of *O. oeni* in quality control winery laboratories.

G. Bleve et al. published in Applied and Environmental Microbiology, July, 2003, p. 4116-4122 that reverse transciptase PCR(RT-PCR) and real-time RT-PCR assays have been used to detect and quantify active mRNA from yeast and moulds. Universal primers were designed based on the available fungal actin sequences, and by RT-PCR they amplified a specific 353 bp fragment from species involved in food spoilage, e.g. rapid detection and quantification of viable yeasts and moulds contaminating yoghurts and pasteurised food products were developed, whereas rapid detection and quantification bacteria as micro-organism using actin mRNA have not been used and described yet.

Maria I. Castellanus et al. reported in Current Microbiology Vol. 33 (1996), pp. 100-103 that three lactic acid bacteria previously selected as probiotic for pig feeding, were identified by sequencing the variable V1 region of the 16 S rDNA after PCR amplification primed in the flanking constant region. A VR region showing strong nucleotide differences between the three probiotic and the reference strains was delimited. Oligonucleotides specific for each strain were designed, because this method is not really suitable for differentiation between living and dead microorganism and therefore not suitable for quantification.

Trevor G. Pfister and David A. Mills published in Applied and Environmental Microbiology, December 2003, p. 7430-7434, a Real-time PCR assay for detection and enumeration of spoilage yeast *Dekkera bruxellensis* in wine without using and describing actin mRNA as target gene, because it is well known that mRNA of ribosomal genes do have a long half-life period.

Casey, Garrett D. et al discloses in International Journal of Food Microbiology 91, 15 Mar. 2004, 327-335, a Real-Time PCR method for detecting and identifying spoilage yeast, such as *Saccharomyces cerevisiae* in fruit-juice based on the 5.85 rDNA and the adjacent ITS 2 region of these yeasts without using and describing mRNA as target gene. Furthermore the described method is not really suitable to differ between living and dead microorganism, because as already said above it is commonly known that mRNA of ribosomal genes do have a long half-life period.

U.S. Pat. No. 6,248,519, Morenzoni Richard A. et al discloses a PCR method for detecting and identifying a fermentation-related microorganism, such as *Saccharomyces cerevisae*, in a beverage sample comprising the steps of obtaining DNA from the sample and detecting *S. bayanus* or *S. cerevisae* by PCR with primers specific for the *S. bayanus* or *S. cerevisae* ITS sequences. This method is also not really suitable for differentiation between living and dead microorganism and therefore not suitable for quantification, because it is known from literature that mRNA ribosomal genes have on the average a long half-life period.

In Database EMBL of Jul. 13, 1992 (1992-07-13) XP002304942 as well as in Database EMBL of Jul. 31, 1991 (1991-07-31) XP002304943 the sequences of *Saccharomyces bayanus* and *Saccharomyces cerevisae* have been described, but not the use thereof.

The publication of D. Kosse et al "Identification of yoghurt-spoiling yeast with 18S rRNAY.targeted oligonucleotide porbes" in Systematic and Applied Microbiology, Vol, 20, 1997, pages 468-480 is mainly to be seen as plain state of the art, not being relevant to the invention.

SUMMARY OF THE INVENTION

The invention is directed towards a method of detecting and identifying germ contaminations or yeast organisms in wine, beer and juices, the method comprising:
  extracting from wine, beer and juices
  contacting the DNA sample with a DNA primer pair and probe comprising DNA primer molecules of sufficient length of contiguous nucleotides of gene actin or gene ATPase or homologues thereof
  providing a nucleic acid amplification reaction condition performing said nucleic acid amplification reaction, thereby producing a DNA amplion molecule
  detecting the amplion molecule.

The invention is also directed towards a method of detecting and identifying of a DNA molecule selected from the gene actin and the gene ATPase or homologues thereof in a DNA sample, the method comprising:

extracting from wine, beer and juices contacting the DNA sample with a DNA primer pair and probe comprising DNA primer molecules of sufficient length of contiguous nucleotides of gene actin, or gene ATPase or homologues thereof providing a nucleic acid amplification reaction condition performing said nucleic acid amplification reaction, thereby producing a DNA amplion molecule detecting the amplion molecule.

The invention is also directed towards a test kit for the detection and identification of germ contaminations in wine, beer and juices comprising the primers and probes specific for a target gene of the microbial contaminant, such as *Dekkera bruxellensis*, *Hanseniasporum uvarum*, *Pediococcus damnosus*, *Pediococcus parvulus*, *Pediococcus pentosaceus*, *Lactobacillus brevis*, *Saccharomyces bayanus* and *Saccharomyces* spp. (*S. bayanus*, *S. cerevisiae*, *S. uvarum*).

DESCRIPTION OF VARIOUS AND PREFERRED EMBODIMENTS OF THE INVENTION

A specific assay for probiotic detection was developed, based on a PCR reaction with three primers to identify and detect the three probiotic strains among other LAB, starting from a small quantity of bacteria, each as only one colony. This has not been reported in alcoholic and non-alcoholic beverages, e.g. wines, musts and other juices.

None of the above mentioned methods or derived methods thereof are suitable to detect remaining genomic DNA in the detection methodology as well as to identify living organism, based on DNA level.

Surprisingly it had been found that in none of the above mentioned citations the special combination of defined primer/probe pairs, the optimised DNA extraction has been described to detect the micro-organism with a very selected and sufficient sensitivity and specificity.

In particular, aim of the invention was to develop a special selected process to identify and quantify living organism based on DNA levels by using a very special combination of defined primer/probe pairs and the optimised DNA extraction as mentioned above. This is the core of the invention with very characteristic features.

Moreover the inventive special selected methodology was developed.

Particularly the invention enables rapid detection and enumeration within 12 hours or less of desired and undesired micro-organism in food and alcoholic and non-alcoholic beverages, e.g. wine, must and other fruit-juices. Furthermore the selection of suitable target genes as molecular markers with the option of applicability with regard to the detection of living and dead micro-organism, this method being superior all known methods of prior art.

Special parts of the invention, for example the claimed procedure or test-kit is a special selected execution of the fluorescence PCR technology (Taq Man®) for the above mentioned target organism.

The invention claims reagents, methods, procedures and application of substances as a special selection that allow the detection, identification and rapid quantification of the above listed micro-organism, such as *Dekkera bruxellensis* (*Brettanomyces*), *Hanseniaspora uvarum*, *Lactobacillus brevis*, *Lactobacillus plantarum*, *Lactobacillus hilgardii* and *Pediococcus damnosus*, *Pediococcus parvulus*, and *Pediococcus pentosaceus* and others which are potential contaminants in wine and other beverages as undesired micro-organism and *Saccharomyces cerevisiae*, *Saccharomyces bayanus*, and *Oenococcus oeni* and others which are desired micro-organism. The invention also embraces test kits, as mentioned above, consisting of primers and probes homologues to the Actin, respectively ATPase sequences. These invented kits allow the correct identification and quantification food relevant yeast and bacteria applying PCR (Polymerase Chain Reaction), respectively real-time PCR.

The applicability of the target sequences have been successfully demonstrated as described above, for example for *Saccharomyces cerevisiae*, *Saccharomycs bayanus*, *Oenococcus oeni*, *Hanseniaspora uvarum*, *Dekkera bruxellensis* (*Brettanomyces*), *Lactobacillus brevis*, *Lactobacillus hilgardii*, *Pediococcus damnosus*, *Pediococcus parvalus* and *Pediococcus pentasaceus* in alcoholic and non-alcoholic beverages, e.g. in wine, musts and other juices. Kits ready for use are for example prepared by using three or more different parts:

The process and test-kit according to the invention are superior in many points to those mentioned previously as prior art, e.g. like microscopy or the so-called fast-detection kits and shall be able to replace these methods completely after validation of the procedure with the particular test product.

The invented method has the following advantages:

The new process (methods) disposes a considerable inventive height in comparison with the known methods for the detection of living and dead micro-organism. Especially the inventive process (methods) or the available test-kits are reacting faster with superior specificity or sensitivity and are useful for the detection of the total amount of living and dead micro-organism.

For the first time it is possible to detect the desired or contaminating micro-organisms *Dekkera bruxellensis* (*Brettanomyces*), *Hanseniaspora uvarum*, *Lactobacillus brevis*, and *Pediococcus damnosus*, *Pediococcus parvulus*, and *Pediococcus pentosaceus*, *Saccharomyces cerevisiae*, *Saccharomyces bayanus*, and *Oenococcus oeni* and others without using a microscope or precedent cultivation that are expressing genes.

In doing so, only *Dekkera bruxellensis* (*Brettanomyces*), *Hanseniaspora uvarum*, *Lactobacillus brevis*, and *Pediococcus damnosus*, *Pediococcus parvulus*, and *Pediococcus pentosaceus Saccharomyces cerevisiae*, *Saccharomyces bayanus* and *Oenococcus oeni* that do express genes (which means living organism compared to living and dead organism to were possible to detect applying previous methods) are registered quantitative and precise with a sensitivity of 1-100 fungi or bacteria respectively in the product investigated.

The consequence of applying the new inventive methodology means higher safeties during the ripening of the wine, as *Dekkera bruxellensis* (*Brettanomyces*), *Hanseniaspora uvarum*, *Lactobacillus brevis*, and *Pediococcus damnosus*, *Pediococcus parvulus*, and *Pediococcus pentosaceus*, *Saccharomyces cerevisiae*, *Saccharomyces bayanus* and *Oenococcus oeni* which is difficult to cultivate can be easily detected. Furthermore the results are available in a much shorter time period compared to the fastest detection method known up till now. All these factors lead to cheaper and qualitative superior products. On top of this no special safety requirements are needed as no components of the used kit underlies a safety regulation.

It was shown above, when prior art has been discussed that the enumeration of cells by real-time PCR has a very high correlation with the enumeration of cells performed with classical microbiological methods. In order to meet this requirements genes were chosen, which are constitutively expressed and which have fundamental attributes in the live cycle of the micro-organisms.

| Detected organism | Target gene |
|---|---|
| Dekkera bruxellensis | Actin gene |
| Hanseniaspora uvarum | Actin gene |
| Pediococcus damnosus | ATPase gene |
| Pediococcus parvulus | ATPase gene |
| Pediococcus pentosaceus | ATPase gene |
| Lactobacillus brevis | ATPase gene |
| Lactobacillus hilgardii | ATPase gene |
| Oenococcus oeni | ATPase gene |
| Saccharomyces bayanus | Actin gene |
| Saccharomyces cerevisiae | Actin gene |

Definitions of some expressions used in the descriptive part of this application are:

A primer is a molecule which has at a polymer matrix a number of nucleotides. The sequence of the nucleotides is chosen in this way that there is more than 90% of homology to the sequence of the amplicon which has to be amplified. The molecule has at least one prolongable end. The term prolongation means the adding of nucleotides with the help of enzymes. As enzyme, preferably a DNA polymerase is used.

The nucleic acid which should be amplified serves as matrix for the specific integration of nucleotides.

The sequence of the matrix determines the sequence of the nucleotides which are added to the primer. Primers are usually used which have a length between 15 and 30 bases. The 3' end of the primer is optimal for the prolongation and therefore preferred.

A probe is a molecule that has as a primer a polymer matrix with a number of nucleotides. For designing a probe the teaching described in U.S. Pat. No. 5,210,015 is used.

The specific sequences are obtained by searching for a sequence of at least 13 bases of the matrix. This sequence has to be in between the two primers. The probe should show at least 90% of homology to the particular matrix. It is much more advisable if probes show a higher degree of homology.

The yeast strains mentioned herein before are common in the food and beverage manufacture, especially well known in the wine manufacturing industry and are well described in literature and need not to be described furthermore in its detail.

PCR reagents are substances which are important for a PCR with a maximum of sensitivity and specificity. Above all these are for example substances like DNA polymerase, $Mg^{2+}$ ions, potassium salts, additives (glycerine, DMSO or formamide), primers, probes, desoxynucleotide, buffers (tri base) and fluorescence dyes.

The invention ultimately allows replacing very effectively the conventional method for testing total viable count and absence or presence of *Dekkera bruxellensis* (*Bretannomyces*), *Hanseniaspora uvarum*, *Lactobacillus brevis*, *Lactobacillus hilgardii*, *Pediococcus damnosus*, *Pediococcus parvulus*, *Pediococcus pentosaceus*, *Saccharomyces cerevisiae*, *Saccharomyces bayanus*, and *Oenococcus oeni*.

The task will be solved by applying a method for the detection of the above mentioned micro-organism for example in food, wine, must or other alcoholic and non-alcoholic beverages containing at least a DNA fragment. The chosen DNA targets are expressed in living micro-organisms. Therefore they are convenient for the detection of alive micro-organisms.

The DNA is detected by applying the following SEQ ID and spacer contains:
(a) the whole amplicon (SEQ ID complete amplicon)
(b) a forward primer (SEQ ID forward)
(c) a probe (SEQ ID probe)
(d) a reverse primer (SEQ ID reverse)
(e) if necessary a spacer between forward primer and probe
(f) if necessary a spacer between probe and reverse primer
(g) if necessary a spacer upstream of the forward primer (h) if necessary a spacer downstream of the reverse primer whereas SEQ ID (SEQ ID forward primer, SEQ ID probe and SEQ ID reverse primer) can include variants, where one, two or more nucleotides are substituted, deleted and/or inserted and all variants set on the same target gene:

in doing so the variant has in general the same function as the sequence of SEQ ID (SEQ ID forward primer, SEQ ID probe and SEQ ID reverse primer) meaning the function of DNA-binding of the probe and DNA and delivering of a prolongable 3'-end for the DNA-polymerase of the primers.

The fragment taken out of this group:
Specific System:
(i) for *Dekkera bruxellensis*
  SEQ ID No. 1 as complete amplicon
  SEQ ID No. 2 as forward-primer
  SEQ ID No. 3 as MGB probe
  SEQ ID No. 4 as reverse primer
(ii) for *Dekkera bruxellensis*
  SEQ ID No. 5 as complete amplicon
  SEQ ID No. 6 as forward-primer
  SEQ ID NO.7 as TaqMan® probe
  SEQ ID No. 8 as reverse primer
(iii) for *Hanseniaspora uvarum*
  SEQ ID No. 9 as complete amplicon
  SEQ ID No. 10 as forward-primer
  SEQ ID No. 11 as MGB probe
  SEQ ID No. 12 as reverse primer
(iv) for *Hanseniaspora uvarum*
  SEQ ID No. 13 as complete amplicon
  SEQ ID No. 14 as forward-primer
  SEQ ID No. 15 as TaqMan® probe
  SEQ ID No. 16 as reverse primer
(v) for *Pediococcus damnosus*
  SEQ ID No. 17 as complete amplicon
  SEQ ID No. 18 as forward-primer
  SEQ ID No. 19 as TaqMan® probe
  SEQ ID No. 20 as reverse primer
(vi) for *Pediococcus parvulus*
  SEQ ID No. 21 as complete amplicon
  SEQ ID No. 22 as forward-primer
  SEQ ID No. 23 as TaqMan® probe
  SEQ ID No. 24 as reverse primer
(vii) for *Pediococcus pentosaceus*
  SEQ ID No. 25 as complete amplicon
  SEQ ID No. 26 as forward-primer
  SEQ ID No. 27 as TaqMan® probe
  SEQ ID No. 28 as reverse primer
(viii) for *Lactobacillus brevis*
  SEQ ID No. 29 as complete amplicon
  SEQ ID No. 30 as forward-primer
  SEQ ID No. 31 as TaqMan® probe
  SEQ ID No. 32 as reverse primer
(ix) for *Lactobacillus hilgardii*
  SEQ ID No. 33 as complete amplicon
  SEQ ID No. 34 as forward-primer
  SEQ ID No. 35 as TaqMan® probe
  SEQ ID No. 36 as reverse primer (x) for *Saccharomyces bayanus*
  SEQ ID No. 37 as complete amplicon
  SEQ ID No. 38 as forward-primer
  SEQ ID No. 39 as TaqMan® probe
  SEQ ID No. 40 as reverse primer
(xi) for *Saccharomyces bayanus*
  SEQ ID No. 41 as complete amplicon
  SEQ ID No. 42 as forward-primer
  SEQ ID No. 43 as MGB probe
  SEQ ID No. 44 as reverse primer Favoured is the application of a kit with PCR reagents. Even more favoured is the application of a kit with PCR reagents and TaqMan® technology. The sequences mentioned are listed in SEQ ID No. 1 to SEQ ID No. 44. For a successful TaqMan® PCR of the DNA fragments as short as possible have to be chosen. This improves and enlarges the possibilities of choosing primers and probes on the target fragment. Amplification of small fragments allows an easier determination of specific Systems. Besides normal TaqMan® probes, the invention includes as well Minor Groove Binder (MGB) with dark quencher.

The following demands are:
  primer have to be between 15 to 30 base pairs long
  the sequence of the probe has to be between the primer sequences on the amplifiable DNA
  the TaqMan® probes have to be between 15 and 30 bases long
  the Minor Groove Binder probes have to be between 14 and 20 base pairs long
  the probe should contain a GC-content of 40 to 60%
  the melting temperature of the probe have to be 8 to 12° C. above the primer
  there should be no G at the 5'-end of the probe
  the sequence of the probe should not contain more than 3 times the same bases in a row
  there should be no complementary sequence between primer and probe or within the primers and no noticeable secondary structure within primers and probe.

In spite of the general guidelines for the design of primer and probe (Livak et al. 1995) the optimal combination of primer and probe of each TaqMan® PCR application has to be experimentally determined.

First it could be shown in a series of experiments that the development of an optimal TaqMan® PCR System was not possible although all the above mentioned guidelines have been followed. Second, it is sometimes necessary because of the characteristics of the target sequence of the corresponding organisms (e.g. high GC-content, highly repetitive elements or conserved regions of sequences) to choose primer and probe sequences that do not fulfil the above mentioned guidelines for the design of the Systems. Consequence of the limitation to the guidelines is that for the achievement of the necessary specificity and sensitivity of a Taqman® PCR test the choice of the diagnostic target sequence in the genome of the micro-organism to determine and the experimental determination of optimal primer and probe sequences are essential conditions including TaqMan® buffer:

The specificity and sensitivity of a TaqMan®-PCR test will be determined beside of the sequence of primer and probe of the following parameter:
  denaturation temperature of the first PCR cycle
  annealing temperature during the amplification phase
  number of PCR cycles
  use of PCR additives as e.g. glycerine and/or formamide
  use of 7-deaza-2-deoxy-GTP beside GTP in genes with a high G/C-content
  concentration of $Mg^{2+}$ ions in the PCR buffer
  concentration of primers and probe
  units of Taq DNA-polymerase
  distance of the cis-oriented primers to the probe.

All these parameters were considered during the development of the described TaqMan® PCR tests.

Nucleic acids that are used as diagnostic targets are: Under the term nucleic acid, which has been used applying the reverse transcription step followed by the amplification procedure and the detection for the target organisms mentioned above, is seen genomic DNA. The genomic DNA sequence includes beside others fragments with sequences, which are characteristic for a species, genus, family or class microorganisms. The DNA sequences can be used in a TaqMan® PCR test as diagnostic target sequence for species, genus, family or class.

There are no especial safety requirements as no components of the kit underlies a safety regulation.

EXAMPLES

Identification of Presence of Microbial Contaminants

The following examples are describing the developed PCR rapid detection kits for the detection of the targets *Dekkera bruxellensis*, *Hanseniaspora uvarum*, *Pediococcus damnosus*, *Pediococcus parvulus*, *Pediococcus pentosaceus*, *Lactobacillus brevis*, *Lactobacillus hilgardii*, *Saccharomyces bayanus*, *Saccharomyces cerevisiae* and *Oenococcus oeni*. Inclusively all sequence variations and target sequences:

| | |
|---|---|
| PCR Conditions | Example 1 |
| Real-time PCR profile | Example 2 |
| Actin gene | Example 3 |
| ATPase gene | Example 4 |
| *Dekkera bruxellensis* | Example 5-7 |
| *Hanseniaspora uvarum* | Example 8-10 |
| *Pediococcus damnosus* | Example 11-13 |
| *Pediococcus parvulus* | Example 14-16 |
| *Pediococcus pentosaceus* | Example 17-19 |
| *Lactobacillus brevis* | Example 20-22 |
| *Lactobacillus hilgardii* | Example 23-25 |
| *Oenococcus oeni* | Example 26-28 |
| *Saccharomyces bayanus* and *Saccharomyces cerevisiae* and *Saccharomyces uvarum* | Example 29-31 |

Example 1

The micro-organisms can be detected according to the table with following PCR conditions (no AmpErase UNG has been used):

| Component | *Dekkera bruxellensis* | *Dekkera bruxellensis* | *Hanseniaspora uvarum* |
|---|---|---|---|
| TaqMan ® 2x Universal PCR Master Mix | 1 x | 1 x | 1 x |
| Primer Forward | 400 nM | 400 nM | 400 nM |
| Primer Reverse | 400 nM | 400 nM | 400 nM |

| | | | |
|---|---|---|---|
| Probe | 100 nM | 100 nM (MGB probe) | 100 nM |
| DNA Sample | 5 µl | 5 µl | 5 µl |
| | Add H$_2$O to 25 µl total Volume | Add H$_2$O to 25 µl total Volume | Add H$_2$O to 25 µl total Volume |

| Component | Hanseniaspora uvarum | Pediococcus damnosus | Pediococcus parvulus |
|---|---|---|---|
| TaqMan ® 2x Universal PCR Master Mix | 1 x | 1 x | 1 x |
| Primer Forward | 400 nM | 900 nM | 900 nM |
| Primer Reverse | 400 nM | 900 nM | 900 nM |
| Probe | 100 nM (MGB probe) | 200 nM | 200 nM |
| DNA Sample | 5 µl | 5 µl | 5 µl |
| | Add H2O to 25 µl total Volume | Add H2O to 25 µl total Volume | Add H2O to 25 µl total Volume |

| Component | Pediococcus pentosaceus | Lactobacillus brevis | Lactobacillus hilgardii |
|---|---|---|---|
| TaqMan ® 2x Universal PCR Master Mix | 1 x | 1 x | 1 x |
| Primer Forward | 900 nM | 300 nM | 300 nM |
| Primer Reverse | 900 nM | 300 nM | 300 nM |
| Probe | 200 nM | 125 nM | 100 nM |
| DNA Sample | 5 µl | 5 µl | 5 µl |
| | Add H2O to 25 µl total Volume | Add H2O to 25 µl total Volume | Add H2O to 25 µl total Volume |

| Component | Oenococcus oeni | S. bayanus, S. uvarum, S. cerevisiae | Saccharomyces cerevisiae |
|---|---|---|---|
| TaqMan ® 2x Universal PCR Master Mix | 1 x | 1 x | 1 x |
| Primer Forward | 100 nM | 900 nM | 900 nM |
| Primer Reverse | 100 nM | 900 nM | 900 nM |
| Probe | 50 nM | 100 nM | 100 nM |
| DNA Sample | 5 µl | 5 µl | 5 µl |
| | Add H2O to 25 µl total Volume | Add H2O to 25 µl total Volume | Add H2O to 25 µl total Volume |

The probes were manufactured by the Company Applied Biosystems, Weiterstadt, Germany. The probe is a single stranded oligonucleotide which was labelled at the 5' end with fluorescence derivate (FAM=6-carboxyfluorescein) and at the 3' end with a fluorescent dye or Minor Groove Binder molecule (MGB). Manufacturing and purification was performed according to the instructions of Applied Biosystems. The primers were manufactured by the Company MWG Biotech, Ebersberg, Germany. The primers are single stranded oligonucleotides which are not modified. Manufacturing and purification was performed according to the instructions of MWG Biotech.

Example 2

Real-Time-PCR Profile

Real-time PCR profile for specific Systems for the detection of *Dekkera bruxellensis, Hanseniaspora uvarum, Pediococcus damnosus, Pediococcus parvulus, Pediococcus pentosaceus, Lactobacillus brevis, Lactobacillus hilgardii, Saccharomyces bayanus, Saccharomyces cerevisiae, Oenococcus oeni* and further micro-organisms.

Incubation of the PCR-plate (Microamp® Optical/96-well reaction plate) in the TaqMan® using the following temperature-time-programme:

| steps | |
|---|---|
| UNG-activity* | 2 min./50° C. |
| activation of AmpliTaq Gold | 10 min./95° C. |
| amplification (45 cycles) | 15 sec./95° C. 60 sec./60° C. |

*Systems to avoid "carry-over"-contamination. Contaminating amplicons are digested before PCR by the enzyme Uracil-N-Glykosylase (UNG).

Example 3

*Dekkera bruxellensi, Hanseniaspora uvarum, Saccharomyces bayanus* and *Saccharmocyces cerevisiae* can be detected in wine, beer and liquor to the according sequence of the Actin target gene, which is part of this application. Specific areas of the Actin gene served as diagnostical target for the development of a rapid detection kit for the detection of *Dekkera bruxellensis, Hanseniaspora uvarum, Saccharomyces bayanus* and *Saccharomyces cerevisiae*. Why was this gene selected as a diagnostical target? In contrast to higher eukaryotes, yeast produces a unique actin molecule encoded by a single gene. The sequence is highly conserved not only between yeast species but in comparison to other known sequences. The actin gene is a housekeeping gene, which plays a mayor role in the live cycle of the *Dekkera bruxellenis, Hanseniaspora uvarum, Saccharomyces bayanus* and *Saccharomyces cerevisiae* organisms.

Therefore it was chosen to serve as a genetic marker to detect the yeast specie *Dekkera bruxellensis, Hanseniaspora uvarum, Saccharomyces bayanus* and *Saccharomyces cerevisiae*.

Example 4

*Pediococcus damnosus, Pediococcus parvulus, Pediococcus pentosaceus, Lactobacillus brevis, Lactobacillus hilgardii,* and *Oenococcus oeni* can be detected in wine, beer and liquor to the according sequence of the ATPase target gene, which is part of the patent.

Specific areas of the ATPase gene served as diagnostical target for the development of a rapid detection kit for the detection of *Pediococcus damnosus, Pediococcus parvulus, Pediococcus pentosaceus, Lactobacillus brevis, Lactobacillus hilgardii,* and *Oenococcus oeni*. Why was this gene selected as a diagnostical target?

The ATPase gene is a housekeeping gene, which is present in mayor energy pathways of cells. Only alive cells are producing ATPase. With this attribute high levels of ATPase are only expected in viable organisms. Therefore it was chosen to serve as a genetic marker to detect the bacterial specie *Pediococcus damnosus, Pediococcus parvulus, Pediococcus pentosaceus, Lactobacillus brevis, Lactobacillus hilgardii,* and *Oenococcus oeni*.

Example 5

Due to DNA sequence comparison, practical optimisation work and use of different primer and probe combinations following Actin DNA sequences were determined as the optimal primer and probe combination for *Dekkera bruxellensis*:

```
Forward primer sequence:
5' TGTCAGAGACATCAAGGAGAAGCT 3'

Probe:
5'- FAM TGTTACGTTGCTTTGGAC - MGB -3'

Reverse primer sequence:
5' CGTCTGCATTTCCTGGTCAA 3'
```

Example 6

Selectivity of the *Dekkera bruxellensis* PCR detection test to evaluate the selectivity of the PCR test specific for *Dekkera bruxellensis*, DNA was extracted from different organisms. The DNA was used to perform a fluorescence PCR Test. The amount of amplified PCR products was listed as the Ct value (Threshold Cycle) in following table:

List of the tested cDNA samples:

| Organism | Accession | Result (as Ct value) |
|---|---|---|
| Yeast | | |
| *Dekkera bruxellensis* | DSM 70739 | 24.2 |
| | Jodat95 | 24.9 |
| | Buess a | 24.4 |
| | Vallellina | 23.9 |
| | Malanser | 23.5 |
| | Cor94-41 | 23.5 |
| *Hanseniaspora uvarum* | DSM 2768 | 45.0 |
| | FAW98/10-4 | 45.0 |
| | FAW75 403H | 45.0 |
| | FAW Rbst-9/00-4 | 45.0 |
| | FAW74 | 45.0 |
| | Rst9/10 | 45.0 |
| *Saccharomyces cerevisiae* | LalvinW15 | 45.0 |
| | Lalvin W27 | 45.0 |
| | Ceppo 20 | 45.0 |
| | DSM 4266 | 45.0 |
| | Lalvin EC 1118 | 45.0 |
| *Saccharomyces bayanus* | FAW 43 | 45.0 |
| *Saccharomyces uvarum* | S6U | 45.0 |
| *Metschnikowia pulcherrima* | Rst6 | 45.0 |
| | DSM 70321 | 45.0 |
| *Pichia anomala* | FAW 10 | 45.0 |
| *Candida stellata* | FAW3 Rst 98/1 0/7 | 45.0 |
| Bacteria | | |
| *Oenococcus oeni* | DSM 20257 | 45.0 |
| *Pediococcus damnosus* | DSM 20331 | 45.0 |
| *Lactobacillus brevis* | DSM 2647 | 45.0 |

Example 7

Sensitivity of the *Dekkera bruxellensis* test to determine the *Dekkera bruxellensis* PCR test, DNA was prepared and deployed in the PCR experiments. Different amounts of DNA of *Dekkera bruxellensis* were deployed in the fluorescence PCR. The number of starting cells for DNA extraction and the Ct values are given in the following table. The Ct values are mean values of six autonomous replications.

| Number of cells/ml for DNA extraction | Mean Ct values |
|---|---|
| $10^7$ | 17.3 |
| $10^6$ | 21.4 |
| $10^5$ | 24.9 |
| $10^4$ | 27.2 |
| $10^3$ | 30.0 |
| $10^2$ | 31.4 |
| $10^1$ | 34.5 |

The result shows that RNA of 100 *Dekkera bruxellensis* cells could be detected in one ml using fluorescence PCR. The PCR detection test allows a linear quantification about 6 log steps, i.e. between $10^2$ and $10^7$ cells/ml.

Example 8

Due to cDNA sequence comparison, practical optimization work and use of different primer and probe combinations following Actin DNA sequences were determined as the optimal primer and probe combination for *Hanseniaspora uvarum*:

```
Forward primer sequence:
5' TCAAAGAAAAGTTATCYTACGTTGCTT 3'

Probe:
5'- FAM AGACTTTGACCAAGAAA - MGB -3'

Reverse primer sequence:
5' TGAAGATTGAGCAGCAGTTTCC 3'
```

Example 9

Selectivity of the *Hanseniaspora uvarum* PCR detection test to evaluate the selectivity of the PCR test specific for

*Hanseniaspora uvarum*, DNA was extracted from different organisms. The DNA was used to perform a fluorescence PCR Test. The amount of amplified PCR products was listed as the Ct value (Threshold Cycle) in following table:

List of the tested DNA samples:

| Organism | Accession | Result (as Ct value) |
|---|---|---|
| Yeast | | |
| *Hanseniaspora uvarum* | DSM 2768 | 22.0 |
| | FAW98/10-4 | 21.3 |
| | FAW75 403H | 20.5 |
| | FAW Rbst-9/00-4 | 20.5 |
| | FAW74 | 21.0 |
| | Rst 9/10 | 22.0 |
| *Dekkera bruxellensis* | DSM 70739 | 45.0 |
| | Jodat95 | 45.0 |
| | Buess a | 45.0 |
| | Vallellina | 45.0 |
| | Malanser | 45.0 |
| | Cor94-41 | 45.0 |
| *Saccharomyces cerevisiae* | Lalvin W15 | 45.0 |
| | Lalvin W27 | 45.0 |
| | Ceppo 20 | 45.0 |
| | DSM 4266 | 45.0 |
| | Lalvin EC 1118 | 45.0 |
| *Saccharomyces bayanus* | FAW 43 | 45.0 |
| *Saccharomyces uvarum* | S6U | 45.0 |
| *Metschnikowia pulcherrima* | Rst6 | 45.0 |
| | DSM 70321 | 45.0 |
| *Pichia anomala* | FAW10 | 45.0 |
| *Candida stellata* | FAW3 | 45.0 |
| | Rst 98/10/7 | 45.0 |
| Bacteria | | 45.0 |
| *Oenococcus oeni* | DSM 20257 | 45.0 |
| *Pediococcus damnosus* | DSM 20331 | 45.0 |
| *Lactobacillus brevis* | DSM 2647 | 45.0 |

Example 10

Sensitivity of the *Hanseniaspora uvarum* test to determine the *Hanseniaspora uvarum* PCR test, DNA was prepared and deployed in the PCR experiments.

Different amounts of DNA of *Hanseniaspora uvarum* were deployed in the fluorescence PCR. The number of starting cells for DNA extraction and the Ct values are given in the following table. The Ct values are mean values of six autonomous replications.

| Number of cells/ml for DNA extraction | Mean Ct values |
|---|---|
| $10^7$ | 18.7 |
| $10^6$ | 22.0 |
| $10^5$ | 25.4 |
| $10^4$ | 29.1 |
| $10^3$ | 32.1 |
| $10^2$ | 35.5 |
| $10^1$ | 40.6 |

The result shows that DNA of 100 *Hanseniaspora uvarum* cells could be detected in one ml using fluorescence PCR. The PCR detection test allows a linear quantification about 6 log steps, i.e. between $10^2$ and $10^7$ cells/ml.

Example 11

Due to DNA sequence comparison, practical optimization work and use of different primer and probe combinations following ATPase DNA sequences were determined as the optimal primer and probe combination for *Pediococcus damnosus*:

```
Forward primer sequence:
5' AGG AAT GGA TGA ATT GTC TGA TGA 3'

Probe:
5'- FAM ATC GTT GGA CGT GCT CGT AGA ATT CAG TTC -
TAMRA -3'

Reverse primer sequence:
5' GCA ACA GAG AAA TTC TGT GAC AAG A 3'
```

Example 12

Selectivity of the *Pediococcus damnosus* PCR detection test to evaluate the selectivity of the PCR test specific for *Pediococcus damnosus*, DNA was extracted from different organisms. The DNA was used to perform a fluorescence PCR Test. The amount of amplified PCR products was listed as the Ct value (Threshold Cycle) in following table:

List of the tested DNA samples:

| Organism | Accession | Result (as Ct value) |
|---|---|---|
| *Pediococcus damnosus* | DSM 20331 | 21.2 |
| *Pediococcus parvulus* | DSM 20332 | 45.0 |
| *Pediococcus pentosaceus* | DSM 20336 | 45.0 |
| *Oenococcus oeni* | DSM 20257 | 45.0 |
| *Lactobacillus brevis* | DSM 2647 | 45.0 |
| *Lactobacillus hilgardii* | DSM 20051 | 45.0 |
| *Lactobacillus plantarum* | DSM 20174 | 45.0 |
| *Saccharomyces cerevisiae* | DSM 4266 | 45.0 |
| *Hanseniaspora uvarum* | DSM 2768 | 45.0 |
| *Brettanomyces bruxellensis* | DSM 70739 | 45.0 |
| *Zygosaccharomyces bailii* | Isolat FAW 210 | 45.0 |
| *Pichia anomala* | CBS 6866 | 45.0 |

Example 13

Sensitivity of the *Pediococcus damnosus* test to determine the *Pediococcus damnosus* PCR test, DNA was prepared and deployed in the PCR experiments.

Different amounts of DNA of *Pediococcus damnosus* were deployed in the fluorescence PCR. The number of starting cells for DNA extraction and the Ct values are given in the following table. The Ct values are mean values of six autonomous replications.

| Number of cells/ml for DNA extraction | Mean Ct values |
|---|---|
| $10^7$ | 21.2 |
| $10^6$ | 24.6 |
| $10^5$ | 28.2 |
| $10^4$ | 31.8 |
| $10^3$ | 35.0 |
| $10^2$ | 38.5 |

The result shows that DNA of 100 *Pediococcus damnosus* cells could be detected in one ml using fluorescence PCR. The PCR detection test allows a linear quantification about 6 log steps, i.e. between $10^2$ and $10^7$ cells/ml.

Example 14

Due to DNA sequence comparison, practical optimisation work and use of different primer and probe combinations following ATPase DNA sequences were determined as the optimal primer and probe combination for *Pediococcus parvulus*:

```
Forward primer sequence:
5' TCA AGA AAC CAG ACG GCA GTA TT 3'

Probe:
5'-FAM TGG TTG CTG AAG TCG CTC TTG - TAMRA -3'

Reverse primer sequence:
5' CAC AAC GCC GTC TCC AAG T 3'
```

Example 15

Selectivity of the *Pediococcus parvulus* PCR detection test to evaluate the selectivity of the PCR test specific for *Pediococcus parvulus*, DNA was extracted from different organisms. The DNA was used to perform a fluorescence PCR Test. The amount of amplified PCR products was listed as the Ct value (Threshold Cycle) in following table:

List of the tested DNA samples:

| Organism | Accession | Result (as Ct value) |
| --- | --- | --- |
| *Pediococcus parvulus* | DSM 20331 | 18.3 |
| *Pediococcus damnosus* | DSM 20332 | 45.0 |
| *Pediococcus pentosaceus* | DSM 20336 | 45.0 |
| *Oenococcus oeni* | DSM 20257 | 45.0 |
| *Lactobacillus brevis* | DSM 2647 | 45.0 |
| *Lactobacillus hilgardii* | DSM 20051 | 45.0 |
| *Lactobacillus plantarum* | DSM 20174 | 45.0 |
| *Saccharomyces cerevisiae* | DSM 4266 | 45.0 |
| *Hanseniaspora uvarum* | DSM 2768 | 45.0 |
| *Brettanomyces bruxellensis* | DSM 70739 | 45.0 |
| *Zygosaccharomyces bailii* | Isolat FAW 210 | 45.0 |
| *Pichia anomala* | CBS 6866 | 45.0 |

Example 16

Sensitivity of the *Pediococcus parvulus* test to determine the *Pediococcus parvulus* PCR test, DNA was prepared and deployed in the PCR experiments.

Different amounts of DNA of *Pediococcus parvulus* were deployed in the fluorescence PCR. The number of starting cells for DNA extraction and the Ct values are given in the following table. The Ct values are mean values of six autonomous replications.

| Number of cells/ml for DNA extraction | Mean Ct values |
| --- | --- |
| $10^7$ | 18.3 |
| $10^6$ | 21.6 |
| $10^5$ | 24.1 |
| $10^4$ | 28.0 |
| $10^3$ | 32.1 |
| $10^2$ | 35.3 |

The result shows that DNA of 100 *Pediococcus parvulus* cells could be detected in one ml using fluorescence PCR. The PCR detection test allows a linear quantification about 6 log steps, i.e. between $10^2$ and $10^7$ cells/ml.

Example 17

Due to DNA sequence comparison, practical optimisation work and use of different primer and probe combinations following ATPase DNA sequences were determined as the optimal primer and probe combination for *Pediococcus pentosaceus*:

```
Forward primer sequence:
5' CTA TCG ATG GCG GCA AAG A 3'

Probe:
5'-FAM CTT GGC CCC GAT ATA AAA CGC G - TAMRA -3'

Reverse primer sequence:
5' GGT GGA TCA CGA TGG ATT 3'
```

Example 18

Selectivity of the *Pediococcus pentosaceus* PCR detection test to evaluate the selectivity of the PCR test specific for *Pediococcus pentosaceus*, DNA was extracted from different organisms. The DNA was used to perform a fluorescence PCR Test. The amount of amplified PCR products was listed as the Ct value (Threshold Cycle) in following table:

List of the tested DNA samples:

| Organism | Accession | Result (as Ct value) |
| --- | --- | --- |
| *Pediococcus pentosaceus* | DSM 20331 | 19.8 |
| *Pediococcus damnosus* | DSM 20332 | 45.0 |
| *Pediococcus parvulus* | DSM 20336 | 45.0 |
| *Oenococcus oeni* | DSM 20257 | 45.0 |
| *Lactobacillus brevis* | DSM 2647 | 45.0 |
| *Lactobacillus hilgardii* | DSM 20051 | 45.0 |
| *Lactobacillus plantarum* | DSM 20174 | 45.0 |
| *Saccharomyces cerevisiae* | DSM 4266 | 45.0 |
| *Hanseniaspora uvarum* | DSM 2768 | 45.0 |
| *Brettanomyces bruxellensis* | DSM 70739 | 45.0 |
| *Zygosaccharomyces bailii* | Isolat FAW 210 | 45.0 |
| *Pichia anomala* | CBS 6866 | 45.0 |

Example 19

Sensitivity of the *Pediococcus pentosaceus* test to determine the *Pediococcus pentosaceus* PCR test, DNA was prepared and deployed in the PCR experiments.

Different amounts of DNA of *Pediococcus pentosaceus* were deployed in the fluorescence PCR. The number of starting cells for DNA extraction and the Ct values are given in the following table. The Ct values are mean values of six autonomous replications.

| Number of cells/ml for DNA extraction | Mean Ct values |
| --- | --- |
| $10^7$ | 19.8 |
| $10^6$ | 23.4 |
| $10^5$ | 27.0 |
| $10^4$ | 30.5 |
| $10^3$ | 34.3 |
| $10^2$ | 37.8 |

The result shows that DNA of 100 *Pediococcus damnosus* cells could be detected in one ml using fluorescence PCR. The PCR detection test allows a linear quantification about 6 log steps, i.e. between $10^2$ and $10^7$ cells/ml.

Example 20

Due to DNA sequence comparison, practical optimisation work and use of different primer and probe combinations following ATPase DNA sequences were determined as the optimal primer and probe combination for *Lactobacillus brevis*:

```
Forward primer sequence:
5' GGT GCT TCG ATT TCT GTT CCA 3'

Probe:
5'-FAM CGG TGA CGA TAC CCT TGG TCG GG - TAMRA -3'

Reverse primer sequence:
5' ATC CCC GAG CAC GTT GAA 3'
```

Example 21

Selectivity of the *Lactobacillus brevis* PCR detection test to evaluate the selectivity of the PCR test specific for *Lactobacillus brevis*, DNA was extracted from different organisms. The cDNA was used to perform a fluorescence PCR Test. The amount of amplified PCR products was listed as the Ct value (Threshold Cycle) in following table:

List of the tested cDNA samples:

| Organism | Accession | Result (as Ct value) |
|---|---|---|
| *Lactobacillus brevis* | DSM 2647 | 22.1 |
| *Lactobacillus brevis* | Lb 11 Aa | 22.2 |
| *Lactobacillus brevis* | Lb 15 Ca | 21.9 |
| *Lactobacillus brevis* | Lb 24A | 21.2 |
| *Lactobacillus brevis* | Lb 21E | 22.4 |
| *Oenococcus oeni* | DSM 20257 | 42.2 |
| *Oenococcus oeni* | E 656 | 41.0 |
| *Oenococcus oeni* | E 655 | 40.0 |
| *Oenococcus oeni* | E 528 | 40.9 |
| *Oenococcus oeni* | E 508 | 41.5 |
| *Pediococcus damnosus* | DSM 20331 | 45.0 |
| *Pediococcus damnosus* | Bpe 176 | 45.0 |
| *Pediococcus damnosus* | Bpe 181 | 45.0 |
| *Pediococcus parvulus* | DSM 20332 | 45.0 |
| *Pediococcus parvulus* | Bpe 124 | 45.0 |
| *Pediococcus parvulus* | Bpe 150 | 45.0 |
| *Pediococcus parvulus* | Bpe 160 | 45.0 |
| *Lactobacillus hilgardii* | DSM 20051 | 40.2 |
| *Lactobacillus plantarum* | DSM 20174 | 36.3 |
| *Hanseniaspora uvarum* | DSM 2768 | 45.0 |
| *Brettanomyces bruxellensis* | DSM 70739 | 45.0 |
| *Saccharomydes cerevisiae* | DSM 4266 | 45.0 |

Example 22

Sensitivity of the *Lactobacillus brevis* test to determine the *Lactobacillus brevis* PCR test, DNA was prepared and deployed in the PCR experiments.

Different amounts of DNA of *Lactobacillus brevis* were deployed in the fluorescence PCR. The number of starting cells for DNA extraction and the Ct values are given in the following table. The Ct values are mean values of six autonomous replications.

| Number of cells/ml for DNA extraction | Mean Ct values |
|---|---|
| $10^7$ | 17.9 |
| $10^6$ | 21.5 |
| $10^5$ | 24.6 |
| $10^4$ | 28.0 |
| $10^3$ | 31.6 |
| $10^2$ | 34.4 |

The result shows that DNA of 100 *Lactobacillus brevis* cells could be detected in one ml using fluorescence PCR. The PCR detection test allows a linear quantification about 6 log steps, i.e. between $10^2$ and $10^7$ cells/ml.

Example 23

Due to DNA sequence comparison, practical optimisation work and use of different primer and probe combinations following ATPase DNA sequences were determined as the optimal primer and probe combination for *Lactobacillus hilgardii*:

```
Forward primer sequence:
5' GAT GGT GTT GTG CGA ACG AT 3'

Probe:
5'-FAM CGA TGG ATG GAA CCG ATG GTC TTC G -
TAMRA -3'

Reverse primer sequence:
5' AAT CAG TAT TTT CAA CTT CCA TTC CA 3'
```

Example 24

Selectivity of the *Lactobacillus hilgardii* PCR detection test to evaluate the selectivity of the PCR test specific for *Lactobacillus hilgardii*, DNA was extracted from different organisms. The cDNA was used to perform a fluorescence PCR Test. The amount of amplified PCR products was listed as the Ct value (Threshold Cycle) in following table:

List of the tested cDNA samples:

| Organism | Accession | Result (as Ct value) |
|---|---|---|
| *Lactobacillus hilgardii* | DSM 20051 | 24.8 |
| *Lactobacillus brevis* | Lb 11 Aa | 45.0 |
| *Lactobacillus brevis* | Lb 15 Ca | 45.0 |
| *Lactobacillus brevis* | Lb 24A | 45.0 |
| *Lactobacillus brevis* | Lb 21E | 45.0 |
| *Oenococcus oeni* | DSM 20257 | 45.0 |
| *Oenococcus oeni* | E 656 | 45.0 |
| *Oenococcus oeni* | E 655 | 45.0 |
| *Oenococcus oeni* | E 528 | 45.0 |
| *Oenococcus oeni* | E 508 | 45.0 |
| *Pediococcus damnosus* | DSM 20331 | 45.0 |
| *Pediococcus damnosus* | Bpe 176 | 45.0 |
| *Pediococcus damnosus* | Bpe 181 | 45.0 |
| *Pediococcus parvulus* | DSM 20332 | 45.0 |
| *Pediococcus parvulus* | Bpe 124 | 45.0 |
| *Pediococcus parvulus* | Bpe 150 | 45.0 |
| *Pediococcus parvulus* | Bpe 160 | 45.0 |
| *Lactobacillus plantarum* | DSM 20174 | 45.0 |
| *Hanseniaspora uvarum* | DSM 2768 | 45.0 |
| *Brettanomyces bruxellensis* | DSM 70739 | 45.0 |
| *Saccharomydes cerevisiae* | DSM 4266 | 45.0 |

Example 25

Sensitivity of the *Lactobacillus hilgardii* test to determine the *Lactobacillus hilgardii* PCR test, DNA was prepared and deployed in the PCR experiments.

Different amounts of DNA of *Lactobacillus hilgardii* were deployed in the fluorescence PCR. The number of starting cells for DNA extraction and the Ct values are given in the following table. The Ct values are mean values of six autonomous replications.

| Number of cells/ml for DNA extraction | Mean Ct values |
| --- | --- |
| $10^7$ | 18.3 |
| $10^6$ | 21.8 |
| $10^5$ | 23.6 |
| $10^4$ | 27.6 |
| $10^3$ | 32.4 |
| $10^2$ | 34.5 |

The result shows that DNA of 100 *Lactobacillus hilgardii* cells could be detected in one ml using fluorescence PCR. The PCR detection test allows a linear quantification about 6 log steps, i.e. between $10^2$ and $10^7$ cells/ml.

Example 26

Due to DNA sequence comparison, practical optimisation work and use of different primer and probe combinations following ATPase DNA sequences were determined as the optimal primer and probe combination for *Oenococcus oeni*:

```
Forward primer sequence:
5' TGG ATT GAC TCG TGG CAT GA 3'

Probe:
5'-FAM TGA TAC CGG TGC TCC TAT TGA AGT TCC G -
TAMRA -3'

Reverse primer sequence:
5' CGT CCC AAC GTC GCT TCT 3'
```

Example 27

Selectivity of the *Oenococcus oeni* PCR detection test to evaluate the selectivity of the PCR test specific for *Lactobacillus brevis*, DNA was extracted from different organisms. The cDNA was used to perform a fluorescence PCR Test. The amount of amplified PCR products was listed as the Ct value (Threshold Cycle) in following table:

List of the tested cDNA samples:

| Organism | Accession | Result (as Ct value) |
| --- | --- | --- |
| *Oenococcus oeni* | DSM 20257 | 16.5 |
| *Pediococcus damnosus* | DSM 20331 | 45.0 |
| *Pediococcus damnosus* | Bpe 176 | 45.0 |
| *Pediococcus damnosus* | Bpe 181 | 45.0 |
| *Pediococcus parvulus* | DSM 20332 | 45.0 |
| *Pediococcus parvulus* | Bpe 124 | 45.0 |
| *Pediococcus parvulus* | Bpe 150 | 45.0 |
| *Pediococcus parvulus* | Bpe 160 | 45.0 |
| *Lactobacillus brevis* | DSM 2647 | 45.0 |
| *Lactobacillus brevis* | Lb 11 Aa | 45.0 |
| *Lactobacillus brevis* | Lb 15 Ca | 45.0 |
| *Lactobacillus brevis* | Lb 24A | 42.0 |
| *Lactobacillus brevis* | Lb 21E | 39.9 |
| *Lactobacillus hilgardii* | DSM 20051 | 38.5 |
| *Lactobacillus plantarum* | DSM 20174 | 45.0 |
| *Hanseniaspora uvarum* | DSM 2768 | 45.0 |
| *Brettanomyces bruxellensis* | DSM 70739 | 45.0 |
| *Saccharomydes cerevisiae* | DSM 4266 | 45.0 |

Example 28

Sensitivity of the *Oenococcus oeni* test to determine the *Oenococcus oeni* PCR test, DNA was prepared and deployed in the PCR experiments. Different amounts of DNA of *Oenococcus oeni* were deployed in the fluorescence PCR. The number of starting cells for DNA extraction and the Ct values are given in the following table. The Ct values are mean values of six autonomous replications.

| Number of cells/ml for DNA extraction | Mean Ct values |
| --- | --- |
| $10^8$ | 16.5 |
| $10^7$ | 19.6 |
| $10^6$ | 23.3 |
| $10^5$ | 26.5 |
| $10^4$ | 30.4 |
| $10^3$ | 33.4 |
| $10^2$ | 37.1 |

The result shows that DNA of 100 *Oenococcus oeni* cells could be detected in one ml using fluorescence PCR. The PCR detection test allows a linear quantification about 7 log steps, i.e. between $10^2$ and $10^8$ cells/ml.

Example 29

Due to DNA sequence comparison, practical optimisation work and use of different primer and probe combinations following Actin DNA sequences were determined as the optimal primer and probe combination for *Saccharomyces bayanus*, *Saccharomyces cerevisiae* and *Saccharomyces uvarum*:

```
Forward primer sequence:
5' TTG AGA GTT GCC CCA GAA GAA C 3'

Probe:
5'-FAM ACC CTG TTC TTT TGA C - MGB -3'

Reverse primer sequence:
5' GAG TCA TCT TTT CTC TGT TTG ATT TAG G 3'
```

Example 30

Selectivity of the *Saccharomyces bayanus*, *Saccharomyces cerevisiae* and *Saccharomyces uvarum*. PCR detection test to evaluate the selectivity of the PCR test specific for *Saccharomyces bayanus*, *Saccharomyces cerevisiae* and *Saccharomyces uvarum*. DNA was extracted from different organisms.

The cDNA was used to perform a fluorescence PCR Test. The amount of amplified PCR products was listed as the Ct value (Threshold Cycle) in following table:

List of the tested cDNA samples:

| Organism | Accession | Result (as Ct value) |
|---|---|---|
| Saccharomydes bayanus | | 22.0 |
| Saccharomydes cerevisiae | DSM 4266 | 23.1 |
| Saccharomydes uvarum | | 22.8 |
| Oenococcus oeni | DSM 20257 | 45.0 |
| Pediococcus damnosus | DSM 20331 | 45.0 |
| Pediococcus damnosus | Bpe 176 | 45.0 |
| Pediococcus damnosus | Bpe 181 | 45.0 |
| Pediococcus parvulus | DSM 20332 | 45.0 |
| Pediococcus parvulus | Bpe 124 | 45.0 |
| Pediococcus parvulus | Bpe 150 | 45.0 |
| Pediococcus parvulus | Bpe 160 | 45.0 |
| Lactobacillus brevis | DSM 2647 | 45.0 |
| Lactobacillus brevis | Lb 11 Aa | 45.0 |
| Lactobacillus brevis | Lb 15 Ca | 45.0 |
| Lactobacillus brevis | Lb 24A | 42.0 |
| Lactobacillus brevis | Lb 21E | 39.9 |
| Lactobacillus hilgardii | DSM 20051 | 38.5 |
| Lactobacillus plantarum | DSM 20174 | 45.0 |
| Hanseniaspora uvarum | DSM 2768 | 45.0 |
| Brettanomyces bruxellensis | DSM 70739 | 45.0 |

Example 31

Sensitivity of the *Saccharomyces* spp. test to determine the *Saccharomyces* spp PCR test, DNA was prepared and deployed in the PCR experiments.

The sensitivity tests were performed using *Saccharomyces bayanus* DNA. Different amounts of DNA of *Saccharomyces bayanus* were deployed in the fluorescence PCR. The number of starting cells for DNA extraction and the Ct values are given in the following table. The Ct values are mean values of six autonomous replications.

| Number of cells/ml for DNA extraction | Mean Ct values |
|---|---|
| $10^7$ | 18.6 |
| $10^6$ | 22.1 |
| $10^5$ | 24.9 |
| $10^4$ | 26.8 |
| $10^3$ | 31.4 |
| $10^2$ | 34.7 |

The result shows that DNA of 100 *Saccharomyces bayanus* cells could be detected in one ml using fluorescence PCR. The PCR detection test allows a linear quantification about 6 log steps, i.e. between $10^2$ and $10^7$ cells/ml.

```
Primers and Probes
for Dekkera bruxellensis
SEQ ID No. 1 (5' to 3')/as amplicon
TGTCAGAGACATCAAGGAGAAGCTTTGTTACGTTGCTTTGGACTTTGACC

AGGAAATGCAGACG

SEQ ID No. 2 (5' to 3')/forward primer
TGTCAGAGACATCAAGGAGAAGCT

SEQ ID No. 3 (5' to 3')/as probe
(FAM) TGTTACGTTGCTTTGGAC (MGB)

SEQ ID No. 4 (5' to 3')/as reverse primer
CGTCTGCATTTCCTGGTCAA for Dekkera bruxellensis
SEQ ID No. 5 (5' to 3')/as amplicon
TGTCAGAGACATCAAGGAGAAGCTTTGTTACGTTGCTTTGGACTTTGACC

AGGAA ATGCAGACGGCAGCACAG

SEQ ID No. 6 (5' to 3')/forward primer
TGTCAGAGACATCAAGGAGAAGCT

SEQ ID No. 7 (5' to 3')/as probe
(FAM) TGTTACGTTGCTTTGGACTTTGACCAGGA (TAMRA)

SEQ ID No. 8 (5' to 3')/as reverse primer
CTGTGCTGCCGTCTGCAT for Hanseniaspora uvarum
SEQ ID No. 9 (5' to 3')/as amplicon
TCAAAGAAAAGTTATCYTACGTTGCTTTAGACTTTGACCAAGAAATGGAA

ACTGCTGCTCAATCTTCA

SEQ ID No. 10 (5' to 3')/forward primer
TCAAAGAAAAGTTATCYTACGTTGCTT

SEQ ID No. 11 (5' to 3')/as probe
(FAM) AGACTTTGACCAAGAAA (MGB)

SEQ ID No. 12 (5' to 3')/as reverse primer
TGAAGATTGAGCAGCAGTTTCC for Hanseniaspora uvarum
SEQ ID No. 13 (5' to 3')/as amplicon
AGTCATCACCATTGGTAACGAAAGATTCAGAGCTCCAGAAGCCTTATTCC

AACCTTCCTTTATTGGTTTAGAATCTGCTGG

SEQ ID No. 14 (5' to 3')/forward primer
AGTCATCACCATTGGTAACGAAAG

SEQ ID No. 15 (5' to 3')/as probe
(FAM) TTCAGAGCTCCAGAAGCCTTATTCCAACCT (TAMRA)

SEQ ID No. 16 (5' to 3')/as reverse primer
CCAGCAGATTCTAAACCAATAAAGG for Pediococcus damnosus
SEQ ID No. 17 (5' to 3')/as amplicon
aggaatggatgaattgtctgatgaagagaagacaatcgttggacgtgctc gtagaattcagttcttcttgtcacagaatttctctgttgc SEQ ID No. 18 (5' to 3')/forward primer
AGG AAT GGA TGA ATT GTC TGA TGA SEQ ID No. 19 (5' to 3')/as probe
(FAM) ATCGTTGGACGTGCTCGTAGAATTCAGTTC (TAMRA)

SEQ ID No. 20 (5' to 3')/as reverse primer
GCA ACA GAG AAA TTC TGT GAC AAG A for Pediococcus parvulus
SEQ ID No. 21 (5' to 3')/as amplicon
tcaagaaaccagacggcagtattttggttgctgaagtcgctcttgaactt ggagacggcgttgtg SEQ ID No. 22 (5' to 3')/forward primer
TCA AGA AAC CAG ACG GCA GTA TT SEQ ID No. 23 (5' to 3')/as probe
(FAM) TGG TTG CTG AAG TCG CTC TTG (TAMRA)

SEQ ID No. 24 (5' to 3')/as reverse primer
CAC AAC GCC GTC TCC AAG T
```

-continued for *Pediococcus pentosaceus*
SEQ ID No. 25 (5' to 3')/as amplicon
CTATCGATGGCGGCAAAGAACTTGGCCCCGATATAAAACGCGATCCAATC

CATCGTGATCCACC

SEQ ID No. 26 (5' to 3')/forward primer
CTA TCG ATG GCG GCA AAG A

SEQ ID No. 27 (5' to 3')/as probe
(FAM) CTT GGC CCC GAT ATA AAA CGC G (TAMRA)

SEQ ID No. 28 (5' to 3')/as reverse primer
GGT GGA TCA CGA TGG ATT for *Lactobacillus brevis*
SEQ ID No. 29 (5' to 3')/as amplicon
ggtgcttcgatttctgttccagtcggtgacgataccccttggtcgggtgtt caacgtgctcggggat SEQ ID No. 30 (5' to 3')/forward primer
GGT GCT TCG ATT TCT GTT CCA SEQ ID No. 31 (5' to 3')/as probe
(FAM) CGG TGA CGA TAC CCT TGG TCG GG (TAMRA)

SEQ ID No. 32 (5' to 3')/as reverse primer
ATC CCC GAG CAC GTT GAA for *Lactobacillus hilgardii*
SEQ ID No. 33 (5' to 3')/as amplicon
gatggtgttgtgcgaacgatcgcgatggatggaaccgatggtcttcgtcg tggaatggaagttgaaaatactgatt SEQ ID No. 34 (5' to 3')/forward primer
GAT GGT GTT GTG CGA ACG AT SEQ ID No. 35 (5' to 3')/as probe
(FAM) CGA TGG ATG GAA CCG ATG GTC TTC G (TAMRA)

SEQ ID No. 36 (5' to 3')/as reverse primer
AAT CAG TAT TTT CAA CTT CCA TTC CA for *Saccharomyces bayanus*
SEQ ID No. 37 (5' to 3')/as amplicon
atttggccggtagagatttgactgactacttgatgaagatcttgagtgaa cgtggttactctttctccaccactgctgaaagagaaattgtccgtgacat caaggaaaaactatgttacgtcg SEQ ID No. 38 (5' to 3')/forward primer
ATTTGGCCGGTAGAGATTTGAC SEQ ID No. 39 (5' to 3')/as probe
(FAM) TTGAGTGAACGTGGTTACTCTTTCTCCACCACT (TAMRA)

SEQ ID No. 40 (5' to 3')/as reverse primer
TTG ACT GAA CGT GGT TAC TCT TTC TCC ACC ACT for *Saccharomyces spp* (*S. bayanus*, *S. cerevisiae*,
*S. uvarum*)
SEQ ID No. 41 (5' to 3')/as amplicon
ttg aga gtt gcc cca gaa gaa cac cct gtt ctt ttg act gaa gct cca atg aac cct aaa tca aac aga gaa aag atg act c SEQ ID No. 42 (5' to 3')/forward primer
TTG AGA GTT GCC CCA GAA GAA C SEQ ID No. 43 (5' to 3')/as probe
(FAM) ACC CTG TTC TTT TGA C (MGB)

SEQ ID No. 44 (5' to 3')/as reverse primer
GAG TCA TCT TTT CTC TGT TTG ATT TAG G for *Oenococcus oeni*
SEQ ID No. 45 (5' to 3')/as amplicon
tggattgactcgtggcatgaaggttcttgataccggtgctcctattgaag ttccggttggagaagcgacgttgggacg SEQ ID No. 46 (5' to 3')/forward primer
TGG ATT GAC TCG TGG CAT GA SEQ ID No. 47 (5' to 3')/as probe
(FAM) TGATACCGGTGCTCCTATTGAAGTTCCG (TAMRA)

SEQ ID No. 48 (5' to 3')/as reverse primer
CGT CCC AAC GTC GCT TCT

---

What is claimed is:

1. A method of detecting and identifying yeast organisms in wine, beer and juices, the method comprising:
   extracting from wine, beer and juices a DNA sample
   contacting the DNA sample with a DNA primer pair and probe comprising DNA primer molecules of sufficient length of contiguous nucleotides of a gene for actin or homologues thereof
   providing a nucleic acid amplification reaction condition and performing said nucleic acid amplification reaction, thereby producing a DNA amplion molecule, and detecting the amplion molecule, wherein the yeast organisms is *Dekkera bruxellensis*, wherein primer sequence SEQ ID No. 2 and 4 and probe sequence SEQ ID No.3 are used for detecting and identifying *Dekkera bruxellensis*.

2. A method of detecting and identifying yeast organisms in wine, beer and juices, the method comprising:
   extracting from wine, beer and juices a DNA sample
   contacting the DNA sample with a DNA primer pair and probe comprising DNA primer molecules of sufficient length of contiguous nucleotides of a gene for actin or homologues thereof
   providing a nucleic acid amplification reaction condition and performing said nucleic acid amplification reaction, thereby producing a DNA amplion molecule, and detecting the amplion molecule, wherein the yeast organisms is *Dekkera bruxellensis*, wherein primer sequence SEQ ID No. 6 and 8 and probe sequence SEQ ID No.7 are used for detecting and identifying *Dekkera bruxellensis*.

3. A test kit for the detection and identification of germ contaminations in wine, beer or juices, comprising, in separate containers, primers and probe(s) specific for a target gene of a microbial contaminant, wherein said primers and probe (s) have primer and probe sequences and wherein
   (a) the primer sequences are SEQ ID No. 2 and 4 and the probe sequence is SEQ ID No. 3 for *Dekkera bruxellensis*; or
   (b) the primer sequence are SEQ ID No. 6 and 8 and the probe sequence is SEQ ID No. 7 for *Dekkera bruxellensis*.

4. The test kit of claim 3 comprising the primers and probe of (a) for detecting and identifying *Dekkera bruxellensis*.

5. The test kit of claim 3 comprising the primers and probe of (b) for detecting and identifying *Dekkera bruxellensis*.

* * * * *